(12) United States Patent
Lewis et al.

(10) Patent No.: US 11,053,522 B2
(45) Date of Patent: Jul. 6, 2021

(54) METHODS AND SYSTEMS FOR OBTAINING OIL FROM A STILLAGE COMPOSITION

(71) Applicant: POET Research, Inc., Sioux Falls, SD (US)

(72) Inventors: Stephen M. Lewis, Sioux Falls, SD (US); John C. Keeler, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 345 days.

(21) Appl. No.: 15/762,039

(22) PCT Filed: Sep. 29, 2016

(86) PCT No.: PCT/US2016/054468
§ 371 (c)(1),
(2) Date: Mar. 21, 2018

(87) PCT Pub. No.: WO2017/059083
PCT Pub. Date: Apr. 6, 2017

(65) Prior Publication Data
US 2018/0273988 A1    Sep. 27, 2018

Related U.S. Application Data

(60) Provisional application No. 62/235,807, filed on Oct. 1, 2015.

(51) Int. Cl.
C12P 7/64    (2006.01)
(52) U.S. Cl.
CPC ......... *C12P 7/64* (2013.01); *C12Y 302/01001* (2013.01)

(58) Field of Classification Search
CPC ... A61K 8/66; C12Y 302/01001; C12P 19/14; C12P 2203/00; C12P 7/14; C12P 2201/00; C12P 7/065; C12P 7/64; C12N 9/2411; C12N 9/2414; A21D 8/042; C12M 47/10; C13K 1/02; C11B 3/003; C11B 1/025
See application file for complete search history.

(56) References Cited

U.S. PATENT DOCUMENTS

| | | | | |
|---|---|---|---|---|
| 7,641,928 B2 * | 1/2010 | Jump | ............... | A23K 10/38 |
| | | | | 426/479 |
| 8,173,412 B2 * | 5/2012 | Dale | ............... | C11B 13/00 |
| | | | | 435/271 |
| 8,702,819 B2 | 4/2014 | Bootsma | | |
| 9,061,987 B2 | 6/2015 | Bootsma | | |
| 2008/0257821 A1 * | 10/2008 | Jump | ............... | A23K 10/38 |
| | | | | 210/632 |
| 2009/0269817 A1 | 10/2009 | Lantero | | |
| 2013/0197104 A1 | 8/2013 | Medhekar et al. | | |
| 2014/0134684 A1 | 5/2014 | Johnston et al. | | |
| 2014/0186907 A1 | 7/2014 | Bootsma | | |
| 2014/0206055 A1 | 7/2014 | Ramos et al. | | |
| 2014/0242251 A1 | 8/2014 | Bootsma | | |

FOREIGN PATENT DOCUMENTS

| | | | |
|---|---|---|---|
| WO | 200238786 A1 | 5/2002 | |
| WO | 20090137839 A1 | 11/2009 | |
| WO | 2014209789 A1 | 12/2014 | |

OTHER PUBLICATIONS

Richardson et al., (2002) "A Novel, High Performance Enzyme for Starch Liquefaction", The Journal of Biological Chemistry, 277(29):26501-26507.
"Minimize Your Process Constraints—Maximize Your Opportunities", Fuelzyme, Alpha-Amylase, Brochure, 2012, 4 pages.
Hahn et. al., "Development of an Equilibrium Dialysis Technique for Quantifying Starch-Lipid Complexes", Cereal Chem, vol. 64, No. 2, 1987, pp. 77-80.
Collado, et. al., Accurate Estimation of Sweet potato Amylase Activity by Flour Viscosity Analysis, Journal of Agriculture Food Chem., vol. 47, 1999, pp. 832-835.
Helland, et. al., "Effect of germination time on alpha-amylase production and viscosity of maize porridge", Food Research International 35, 2002, pp. 315-321.
Van Zyl, et. al., Engineering yeasts for raw starch conversion, Appl. Microbiol Biotechnol, published online Jul. 14, 2012, pp. 1-12.
Sievert, et. al., "Enzyme-Resistant Starch, III, X-Ray Diffraction of Autoclaved Amylomaize VII Starch and Enzyme-Resistant Starch Residues", Cereal Chemistry, 68(1) pp. 86-91.
Dickey, et. al., "Modification of aqueous enzymatic oil extraction to increase the yield of corn oil from dry fractionated corn germ", Industrial Crops and Products, 34(2001), pp. 845-850.
Luangthongkam et. al., "Addition of cellulolytic enzymes and phytase for improving ethanol fermentation performance and oil recovery in corn dry grind process", Industrial Crops and Products, 77(2015), pp. 803-898.
Majoni, et. al., "Enzyme Treatments to Enhance Oil Recovery from Condensed Corn Distillers Solubles", Journal of American Oil Chem. Soc, (2011), 88, pp. 523-532.
Mojtaba, et. al., "Optimization of Enzymatic Extraction of Oil from Pistacia Khinjuk Seeds by Using Central Composite Design", Food Science and Technology, 2013, 1(3), pp. 37-43.

(Continued)

*Primary Examiner* — Lynn Y Fan
(74) *Attorney, Agent, or Firm* — Kagan Binder, PLLC (57) ABSTRACT

Provided are methods and systems of obtaining oil from a stillage composition.

18 Claims, 6 Drawing Sheets

(56) References Cited

OTHER PUBLICATIONS

International Search Report for International Application No. PCT/US2016/054468, dated Nov. 14, 2016, (6 pages).
Written Opinion for International Application No. PCT/US2016/054468, dated Nov. 14, 2016, (9 pages).
Hahn et al., "Factors Influencing Corn Starch-Lipid Complexing", Cereal Chem, vol. 64, No. 2, 1987, pp. 81-85.

* cited by examiner

METHODS AND SYSTEMS FOR OBTAINING OIL FROM A STILLAGE COMPOSITION

CROSS-REFERENCE TO RELATED APPLICATIONS & PRIORITY CLAIM

This application claims priority to International Application No. PCT/US2016/054468 filed Sep. 29, 2016, which claims priority to U.S. Provisional Application No. 62/235,807 filed Oct. 1, 2015, which is herein incorporated by reference in its entirety.

BACKGROUND

Various processes for recovering oil from a fermentation product are currently known in the art. There is a continuing need for improved methods and systems that provide oil derived from a fermentation product.

SUMMARY

Disclosed are methods and systems that provide improved processes for obtaining oils from a fermentation production process, such as an ethanol production process. In one aspect of the present application is disclosed a method of obtaining an oil composition from a stillage composition including:
 adding one or more alpha amylase enzymes to a first stillage composition to form a second stillage composition, wherein the one or more alpha amylase enzymes are added to the first stillage composition in an amount from 0.001 to 0.05 grams/100 grams of solids of the first stillage composition; and
 obtaining oil from the second stillage composition.

In another aspect of the present application is disclosed a method of obtaining an oil composition from a stillage composition including:
 separating a whole stillage into a thin stillage and a wet cake;
 evaporating at least a portion of water from the thin stillage to condense the thin stillage into a syrup;
 separating the syrup into a first oil fraction and a first aqueous fraction;
 adjusting pH of the first oil fraction to separate the first oil fraction into a second oil fraction and a second aqueous fraction; and
 separating the second oil fraction and the second aqueous fraction to provide the oil composition; wherein one or more alpha amylase enzymes are added to the whole stillage, thin stillage, wet cake and/or syrup in an amount from 0.001 to 0.05 grams/100 grams of solids of the whole stillage, thin stillage, wet cake and/or syrup.

In still another aspect of the present application is disclosed a system for obtaining oil from a stillage composition including:
 a first separator configured to separate a whole stillage into a first solid component and a first liquid portion;
 an evaporator in fluid communication with a first separator to receive the first liquid portion and configured to condense the first liquid portion;
 a second separator in fluid communication with the evaporator and configured to separate the condensed first liquid portion to a first aqueous fraction and a first oil fraction;
 a source of one or more alpha amylase enzymes in fluid communication with the first separator and second separator, wherein the one or more alpha amylase enzymes are added to the whole stillage, first liquid portion and/or condensed first liquid portion in an amount from 0.001 to 0.05 grams/100 grams of solids to the whole stillage, first liquid portion and/or condensed first liquid portion;
 a source of base in fluid communication with the first oil fraction; and a third separator in fluid communication with the first oil fraction and configured to obtain a second oil fraction from the pH-adjusted first oil fraction.

Disclosed in one aspect of the present application is a method of obtaining an oil composition from a stillage composition including:
 adding one or more alpha amylase enzymes to a first stillage composition to form a second stillage composition, wherein the one or more enzymes are added to the first stillage composition at a pH of less than 4.2; and
 obtaining oil from the second stillage composition.

Disclosed in one aspect is oil that can be obtained from the disclosed methods by adjusting pH of the second stillage composition into a first oil fraction to separate the first oil fraction into a second oil fraction and an aqueous fraction; and separating the second oil fraction and the aqueous fraction to provide the oil composition.

DETAILED DESCRIPTION

Disclosed are methods and systems for an improved process of obtaining oil from the backend of a fermentation process. Fermentation products, such as ethanol, are typically produced by first grinding starch-containing material in a dry-grind or wet-milling process, then degrading the material into fermentable sugars using enzymes and finally converting the sugars directly or indirectly into the desired fermentation product using a fermenting organism. The fermentation product or beer can include ethanol, water, oil, additional soluble components, unfermented particulate matter, and the like. The beer can then be distilled to provide ethanol, leaving the remaining components as whole stillage.

The whole stillage can be separated to provide a liquid component, referred to as thin stillage and a solid component, referred to as wet cake or wet grains. The solid component can be dried to provide the "Distillers Dried Grains" (DDG), whereas the thin stillage can be further processed to provide oil compositions. Thin stillage may be evaporated to provide condensate and syrup or may alternatively be recycled directly to the slurry tank as "backset". The syrup may be blended into DDG or added to the wet cake before drying to produce Distillers Dried Grain with Solubles (DDGS). As used herein, "stillage composition" is used to refer to whole stillage, thin stillage, wet cake and/or syrup. Oil may be obtained from the stillage composition. In some embodiments, oil may be obtained from thin stillage and/or evaporated syrup. The oil may be used in biodiesel production, edible grade oil production (e.g. GRAS certified) or other bio renewable products.

Disclosed herein is a method that includes adding alpha amylase to various stages in the processing and/or production of whole stillage to facilitate recovery of oil.

Figure 1:
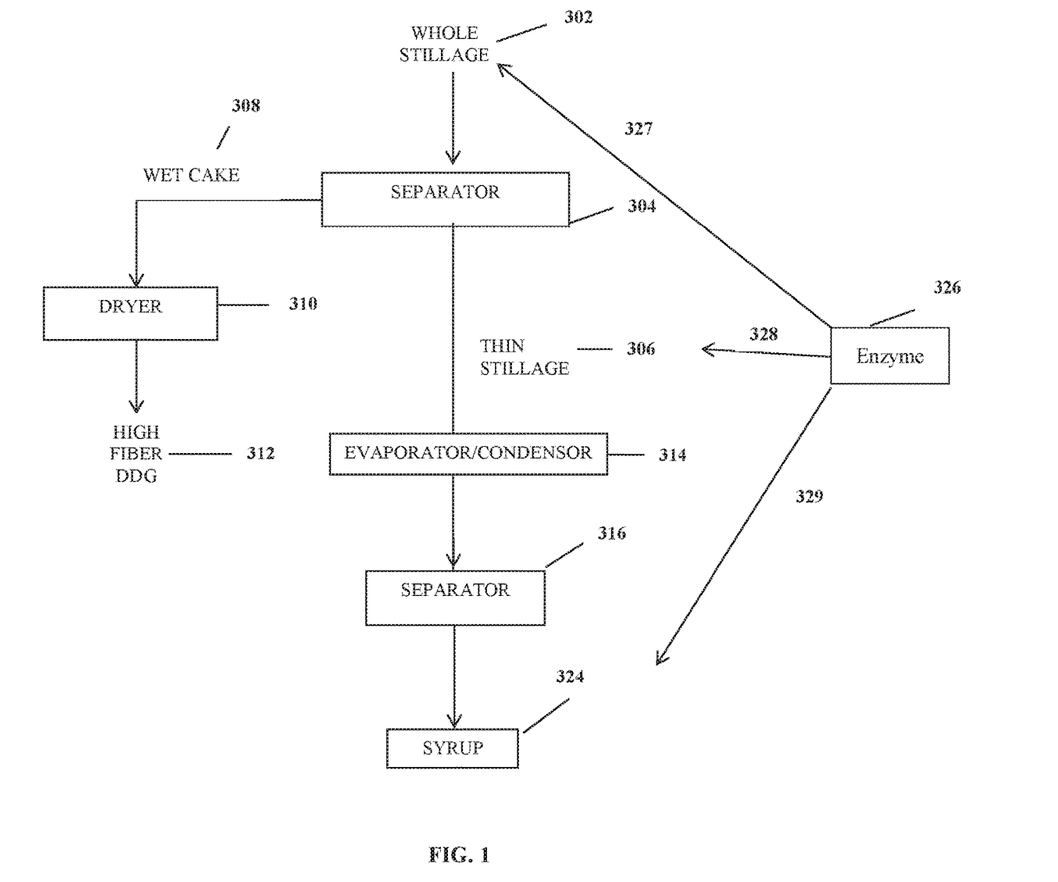
FIG. 1 is a schematic block diagram illustrating an embodiment of a system for fractionating whole stillage.

FIG. 1 shows an example of a system for fractionation of the resultant whole stillage to recover oil that is endogenous to the corn in the feedstock. In this example, the whole stillage 302 is provided to a stillage separator 304 for separation of the stillage into a solids component and a liquid thin stillage 306. The separation may be performed through screw press, centrifugation, decanters, or via filtration type methodologies. In some embodiments, the separation may be performed utilizing a screen bowl centrifuge. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

The solid component or wet cake 308 contains a high fiber cake, which may be dried at a dryer 310 to a high fiber dried distillers grain (DDG) 312 product. Such high fiber DDG 312 may be particularly suited for the polygastric animal feed markets (ruminant feed). In some embodiments, the fiber cake may additionally undergo a washing step prior to being dried. The wash fluid may be combined with the liquid thin stillage, in some embodiments.

Separation of the solid component from the thin stillage may be performed soon after initial production of the fermentation product (whole stillage) to maintain the quality of the oil composition and to prevent undue exposure of the oil composition to heat, oxygen, and potential contaminants. If the whole or thin stillage is left exposed for extended time periods in the presence of moisture, hydrolysis of the oils may occur which leads to the formation of free fatty acids, which degrades the oil quality produced.

The resulting liquid thin stillage 306 is provided to an evaporator 314 or a series of evaporators followed by a separator 316 to condense the thin stillage to syrup 324. The resultant products from the process depicted in FIG. 1, for example, thin stillage, wet cake and/or syrup can be used for obtaining oil. An enzyme can be added at one or more points of processing and production of stillage composition to facilitate the recovery of oil. As shown in FIG. 1, enzyme 326 may be added to the stillage composition at one or more of 327, 328 and 329.

The solids content of the stillage composition can increase the viscosity. High viscosity may limit the efficiency of oil extraction. Therefore, reducing the viscosity of the stillage composition may allow an increased water removal during the evaporation of thin stillage which maintains or increases oil yield. Viscosity reduction may also increase the efficiency of whole stillage separation to wet cake and thin stillage.

Disclosed herein is a process of reducing the viscosity of a stillage composition and/or beer by the addition of an enzyme to a stillage composition and/or beer. One or more alpha amylase enzymes may be added to improve the viscosity of the stillage composition and/or beer.

The reduction in viscosity of the stillage composition and/or beer can result in an improved process of obtaining oil. Without intending to be bound by any theory, the addition of alpha amylase may result in disrupting any complexes such as starch/lipid complexes thereby resulting in reduced viscosity and/or increased oil yield and quality.

The alpha amylase may be added to the beer and/or stillage composition, namely the whole stillage, thin stillage, wet cake and/or syrup. The alpha amylase may be added to stillage composition in the amount from about 0.001 to 0.05 grams/100 grams of solids of the stillage composition. In some embodiments, the alpha amylase may be added as in the range from 0.002 grams/100 grams to 0.04 grams/100 grams of solids of the stillage composition. In other embodiments, the alpha amylase may be added as in the range from 0.005 grams/100 grams to 0.009 grams/100 grams of solids of the stillage composition. In some embodiments, the alpha amylase may be added to the stillage composition in the amount of 0.033 grams/100 grams of solids of the stillage composition. In some embodiments, the alpha amylase may be added to the stillage composition in the amount of 0.015 grams/100 grams of solids of the stillage composition. The alpha amylase used in facilitating the recovery or obtaining the oil from the stillage composition can be a low pH, thermostable enzyme. In some embodiments the alpha amylase may be added to the stillage composition and/or beer at a pH less than 4.2. In other embodiments, the alpha amylase may be added to a stillage composition and/or beer at a pH less than 4.0, or at a pH from about 3.2 to 3.9. The alpha amylase may be added to the stillage composition and/or beer at temperatures from 75° C. to 95° C. In other embodiments, the alpha amylase may be added to the stillage composition and/or beer at a temperature of 80° C. to 90° C. In still other embodiments, the alpha amylase may be added to the stillage composition at a pH of less than 4.2 and at a temperature of 75° C. to 95° C. The alpha amylase used in the fermentation process may differ from the alpha amylase used in the process of obtaining oil.

Exemplary alpha amylases for use in a method of obtaining oil from a stillage composition or a method for reducing viscosity of the stillage composition can include enzymes that are thermostable and work at low pH. Commercially available enzymes include FUELZYME™ (Verenium Corp, part of BASF) and LpHERA™ (Novozymes).

In one embodiment, the thin stillage may have a solids concentration of 6-9 or 7-8% (wt/wt %) of total thin stillage. In some embodiments, the thin stillage may have a solids concentration of 6-9 (wt/wt %) of total thin stillage and the alpha amylase may be added in the amount from 0.01 grams to about 0.04 grams/100 grams of solids of the stillage composition. This dosing rate can reduce the viscosity 20-35%. In other embodiments, the thin stillage may have a solids concentration of 6-9 wt % and the alpha amylase may be added in the amount from 0.003 grams/100 grams to about 0.012 grams/100 grams of solids of the stillage composition can result in a viscosity reduction of about 20-35%. In other embodiments, 0.001 grams/100 grams to about 0.004 grams/100 grams of solids of the stillage composition can reduce the viscosity from 0-10%.

In one embodiment, a method of obtaining oil from a stillage composition is disclosed that includes adding one or more alpha amylase enzymes to a first stillage composition to form a second stillage composition, wherein the one or more enzymes are added in an amount from 0.001 grams/ 100 to 0.05 grams/100 grams of solids of the stillage composition; and obtaining oil from the second stillage composition.

In other embodiments, a method of obtaining an oil composition from a stillage composition includes enzymatically reducing the viscosity of a first stillage composition to form a second stillage composition, wherein the first stillage composition is at a pH of less than 4.2 and at a temperature of 75° C. to 95° C.; and obtaining oil from the second stillage composition.

Figure 2:
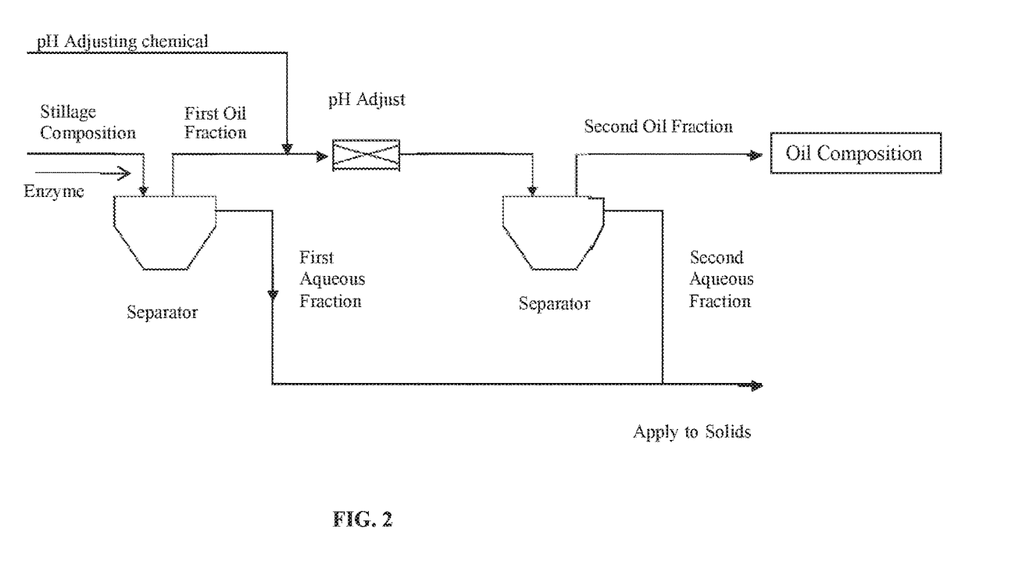
FIG. 2 is a schematic diagram of an embodiment of a system configured to obtain oil from stillage composition.

FIG. 2 depicts a process of obtaining oil. The stillage composition (e.g. thin stillage) may be subjected to a separator. This separation may be accomplished by applying a first centrifugal force to the stillage composition to form a first oil fraction and a first aqueous fraction. The first oil fraction may include an oil-rich emulsion phase and an aqueous phase containing heavy components. The first oil fraction's pH may be adjusted to a level that separates or breaks the first oil fraction thus forming a mixture that includes a second oil fraction having a low fatty acid content and any remaining first oil fraction formed as a result of applying the first centrifugal force. The pH adjustment allows selective separation of higher quality oil while leaving the free fatty acids in an aqueous fraction by saponifying the fatty acids thus making them more water soluble. Thus, a portion of the free fatty acid is removed resulting in oil that contains low levels of free fatty acid. The age of the stillage composition and the organic acid content of the stillage composition can affect the optimum pH for separation; however, the first oil fraction is treated with the highest pH possible to reduce the overall free fatty acid content in the separated oil without sacrificing oil quality. Any remaining stillage composition containing aqueous phase along with any remaining heavy components are removed. The mixture of the first and second oil fractions can be further processed. The method of recovering the oil further includes the step of applying a second centrifugal force to the first oil fraction after adjusting the pH resulting in a second aqueous fraction and a second oil fraction with the resulting oil composition being capable of direct shipment to bio-diesel producers or further refinement to edible oil standards.

In one embodiment, a first centrifugal force is applied to the stillage composition soon after initial production of the stillage composition to maintain oil composition quality and prevent exposure to heat and oxygen. If the stillage composition is left exposed for extended time periods in the presence of moisture, hydrolysis of the oils may occur which leads to free fatty acids formation.

The first centrifugal force, in one embodiment, is applied via a separator or centrifuge or a combination thereof, including, but not limited to, for example, a press, extruder, a decanter centrifuge, a disk stack centrifuge, a screen centrifuge or a combination thereof. In one embodiment, a continuous flow at about 4000 g is maintained. One of ordinary skill in the art will appreciate that the speed or amount of centrifugal force applied will depend on various factors such as sample size and may be adjusted appropriately depending on such factors. Suitable separators and centrifuges are available from various manufacturers such as, for example, Seital of Vicenza, Italy, Westfalia of Oelde, Germany or Alfa Laval of Lund, Sweden.

In one embodiment, a centrifuge, alone, can be used to apply the centrifugal force to the stillage composition. In one embodiment, back pressure is applied to a heavy phase of the resulting oil fraction to improve separation of the oil composition from the aqueous phase and heavy components. A back pressure can be applied by adjusting the centrifuge to restrict the flow of the oil fraction from the centrifuge.

In one embodiment, the method further comprises the step of removing a first aqueous fraction after separating the first oil fraction from the stillage composition. The first aqueous fraction, in one embodiment, includes about 65% to about 95% moisture, based on the total weight of the first aqueous fraction. In one embodiment, the first aqueous fraction includes about 12% to about 40% protein, based on the total weight of the first aqueous fraction. In one embodiment, the first aqueous fraction includes up to about 10% oil, based on the total weight of the first aqueous fraction. In one embodiment, the remainder of the first aqueous fraction includes starch, neutral detergent fiber or a combination thereof. All or a fraction of the first aqueous fraction may be further processed or applied to solids such as, for example, distillers dried grain.

In one embodiment, the pH is adjusted by introducing an inorganic base to the first oil fraction. In one embodiment, the pH is increased. The inorganic base can be divalent or monovalent. Preferably, the inorganic base is a monovalent hydroxide base containing a metal from Group I. Most preferably, the inorganic base can be KOH or NaOH. In one embodiment, the pH of the first oil fraction is adjusted to a range of about 7 to about 10. In other embodiments, the pH is adjusted to a range of about 7.5 to about 9.0, about 8.0 to about 8.5 or about 7.2 to about 8.2.

In one embodiment, the second centrifugal force is applied via a separator or centrifuge or a combination thereof. In one embodiment, a second aqueous fraction is formed upon application of the second centrifugal force. In one embodiment, the second aqueous fraction comprises 60% to 80% moisture, based on the total weight of the second aqueous fraction. In one embodiment, the second aqueous fraction comprises 10% to 40% wt/wt protein, based on the total weight of the second aqueous fraction. In one embodiment, the second aqueous fraction comprises up to 50% oil, based on the total weight of the second aqueous fraction. In one embodiment, the remainder of the second aqueous fraction contains starch, neutral detergent fiber or a combination thereof. The second aqueous fraction can be used to treat distillers dried grain or other solids where an increased level of these components is desirable.

In one embodiment, the method includes the step of recovering the oil composition from the pH-adjusted first oil fraction. In one embodiment, recovering the oil composition includes separating or removing or both separating and removing the second oil fraction from the first oil fraction after adjusting the pH. Recovering the oil composition includes but is not limited to, storage of the oil composition.

In one embodiment, the method includes the step of separating an oil fraction from the stillage composition, wherein the oil fraction contains an oil composition. In one embodiment, the resulting second oil fraction contains from about 20% w/w to about 70% w/w oil. In another embodiment, the second oil fraction contains from about 30% w/w to about 60% w/w oil, or from about 40% w/w to about 50% w/w oil. The oil fraction may also have varying amounts of the stillage composition. In one embodiment, the oil fraction can have about 20% w/w of the initial stillage composition. In any of the aforementioned embodiments, the oil fraction can be an emulsion. In some embodiments, the amount of oil obtained from a stillage composition in which alpha amylase is added can be 15% to 75% more oil than a stillage composition in which no alpha amylase is added. In other embodiments, the amount of oil obtained from a stillage composition in which alpha amylase is added can be 30% to 50% more oil than a stillage composition in which no alpha amylase is added.

The oil composition recovered from the method described herein may be further processed in a variety of ways. For example, the oil composition may be filtered and bleached to provide food grade oil for consumer use. In one embodiment, the oil composition may be degummed, further caustic refined, and subjected to a soap removal step according to commercially available processes. Following these steps the oil may then be subjected to one or more clay bleaching steps to achieve an oil of desired content and color.

In addition to or as an alternative to clay bleaching, after the oil composition has been degummed, caustic refined and subjected to a soap removal step, a food grade oil of a desired color may be achieved using a heat bleaching step. Suitable processes for degumming, caustic refining, and soap removal as described are known by those of ordinary skill in the art. Clay bleaching and heat bleaching processes are also accessible to those of skill in the art and can be utilized to achieve a food grade oil.

The oil composition recovered from the method described herein, in one embodiment, may be used to produce bio-diesel and glycerin. There are several processes that may be used to produce bio-diesel from oils and fats, including base catalyzed transesterification, direct acid catalyzed transesterification, and conversion of the oil to its fatty acids followed by conversion of the fatty acids to bio-diesel. Bio-diesel production technologies and equipment are commercially available from, for example, Crown Iron Works Company of Minneapolis, Minn., U.S.A., and from Lurgi AG of Frankfurt, Germany. To produce bio-diesel and glycerin from the oil composition described herein, a base catalyzed transesterification process may be used. Further processing of the oil composition is disclosed in U.S. Pat. No. 8,702,819, which is hereby incorporated by reference in its entirety.

The stillage composition used to obtain oil may itself be obtained from an ethanol fermentation production process. In one embodiment, the fermentation process can be carried out without creating a hot slurry (i.e., without cooking). In some embodiments, fermentation can be carried out without a liquefaction step. The fermentation process may be carried out with a saccharification step of the starch composition with an enzyme composition to form a saccharified composition (e.g., without cooking). In some embodiments, the enzyme composition used for saccharification can include an alpha amylase and glucoamylase added at a pH from 3 to 6 or at a pH from 4 to 5. In some embodiments the enzyme composition that may be used for saccharification may be added at a temperature from 25° C. to 40° C.

In another embodiment, the fermentation process can be a conventional enzymatic liquefaction process. The starch slurry may be heated to between 50° C. to 100° C. (i.e., cooked), between 60° C. to 90° C. or between 80° C. and 85° C. Next, a thermostable alpha-amylase may be added to initiate liquefaction.

The slurry can then be jet-cooked at a temperature between 100° C. to 145° C. to complete gelatinization of the slurry or between 102° C. to 135° C. or between 105° C. to 125° C. to complete gelatinization of the slurry.

The slurry can be cooled to a temperature between 50° C. to 100° C., between 65° C. to 97° C. or between 60° C. to 95° C. Next, an additional alpha-amylase can be added to finalize hydrolysis. The liquefaction process can be generally carried out at a pH of between about 3 and about 8, between about 4 and about 7 or between about 5 and about 6.

In one embodiment of the conventional enzymatic liquefaction process, the dextrins from the liquefaction may be further hydrolyzed to produce low molecular sugars degree of polymerization 1-3 that can be metabolized by yeast. The hydrolysis may be typically accomplished using glucoamylases, alternatively or in addition to glucoamylases, alpha-glucosidases and/or alpha-amylases can be used. A full saccharification step can last up to 72 hours. In an alternative embodiment, a pre-saccharification step lasting 40-90 minutes at a temperature above 50° C. may be followed by a complete saccharification via a process known as simultaneous saccharification and fermentation (SSF). In one embodiment of the conventional enzymatic liquefaction process, fermentation may be performed using a yeast, e.g., from Saccharomyces spp., which is added to the milled and liquefied whole grains (e.g., mash).

In one embodiment, the starch composition includes water and from 5% to 60% dried solids granular starch, based on the total weight of the starch composition. In another embodiment, the starch composition includes 10 to 50 wt/wt % dried solids granular starch, based on the total weight of the starch composition. In one embodiment, the starch composition includes 15% to 40 wt/wt % dried solids, based on the total weight of the starch composition or about 20% to 25% dried solids granular starch, based on the total weight of the starch composition. The starch can be obtained from various sources such as, for example, plant materials. Suitable plant materials include, but are not limited to, for example, tubers, roots, stems, cobs, leaves, legumes, cereals or whole grain. In one embodiment, the granular starch can be obtained from, for example, corn, cobs, wheat, barley, rye, milo, sago, cassava, tapioca, sorghum, rice, peas, bean, banana or potatoes. In other embodiments, energy grasses such as switchgrass may be used.

In one embodiment, the raw material containing the starch may be milled to open up the structure and allow for further processing. Dry milling as well as wet milling may be used. When wet milling is applied, the steps of soaking or steeping may precede milling. Both dry and wet milling is well known in the art of alcohol manufacturing. Methods for producing alcohol during fermentation are disclosed in U.S. Pat. Nos. 7,842,484 and 7,919,291 and are hereby incorporated by reference in their entirety.

The invention is further illustrated in the following non-limiting examples.

Example 1

Viscosity Reduction

Figure 3:
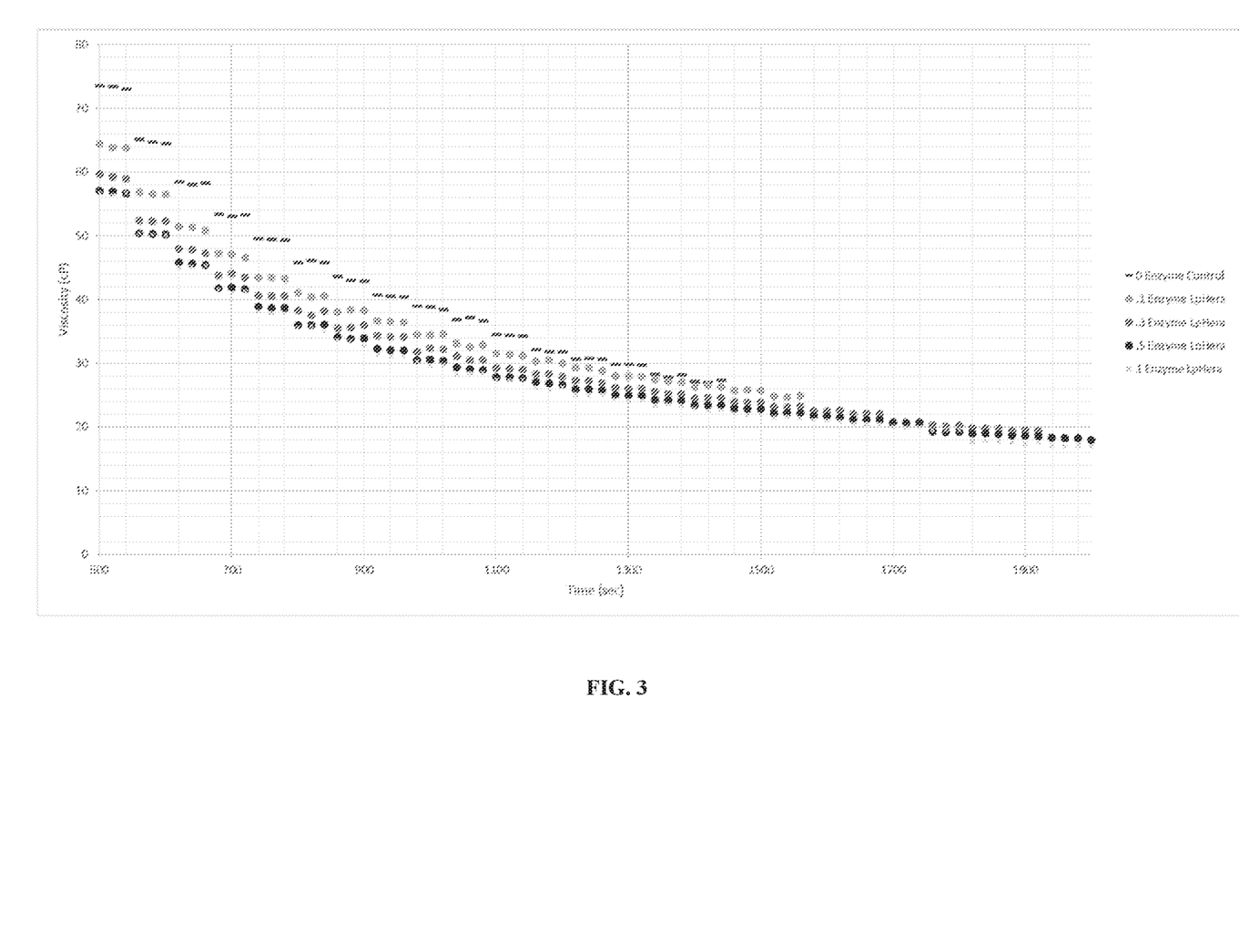
FIG. 3 is a graphical representation of viscosity over time for the enzyme LpHERA™.
Figure 4:
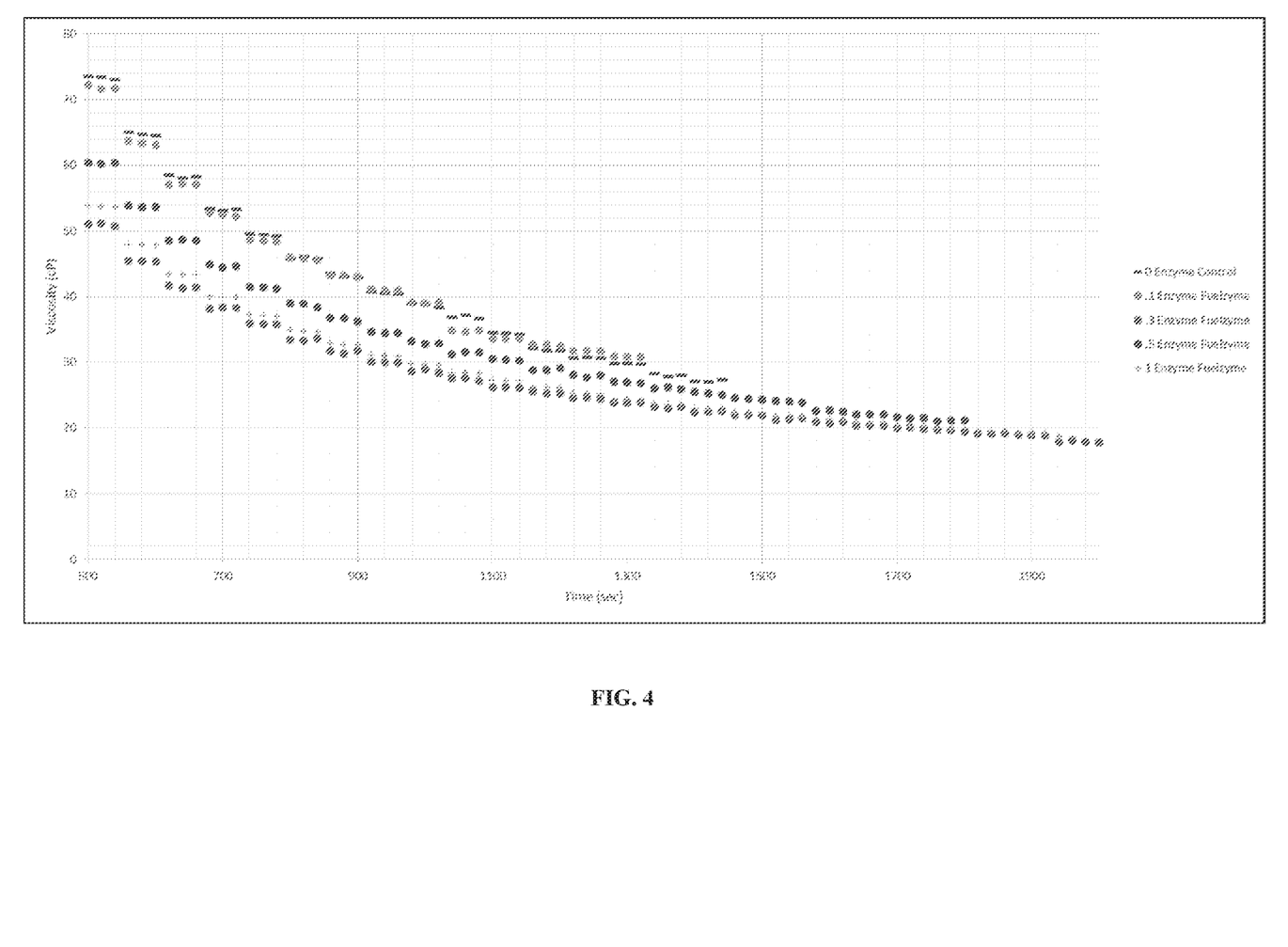
FIG. 4 is a graphical representation of viscosity over time for the enzyme FUELZYMES™.

Alpha amylases of varying amounts were added to whole stillage for 1-24 hours. Alpha amylase, LpHERA™ (Novozymes), was added in the amount of 0.033 gm/100 gm of whole stillage solids, which is considered a 1.0× loading; and FUELZYMES™ (Verenium) was added in the amount of 0.015 gm/100 gm of whole stillage solids, which is considered a 1.0× loading. The whole stillage was obtained from a BPX™ process, dry grind, corn ethanol biorefinery. The viscosity of the samples was measured by a Brookfield Viscometer at various times within a 1-4 hour time range after the alpha amylase was added. The viscosity of the samples were evaluated and plotted over time and shown in FIG. 3 and FIG. 4. The plots below show viscosity reductions by the addition of alpha amylase.

Example 2

Oil Yield

Figure 5:
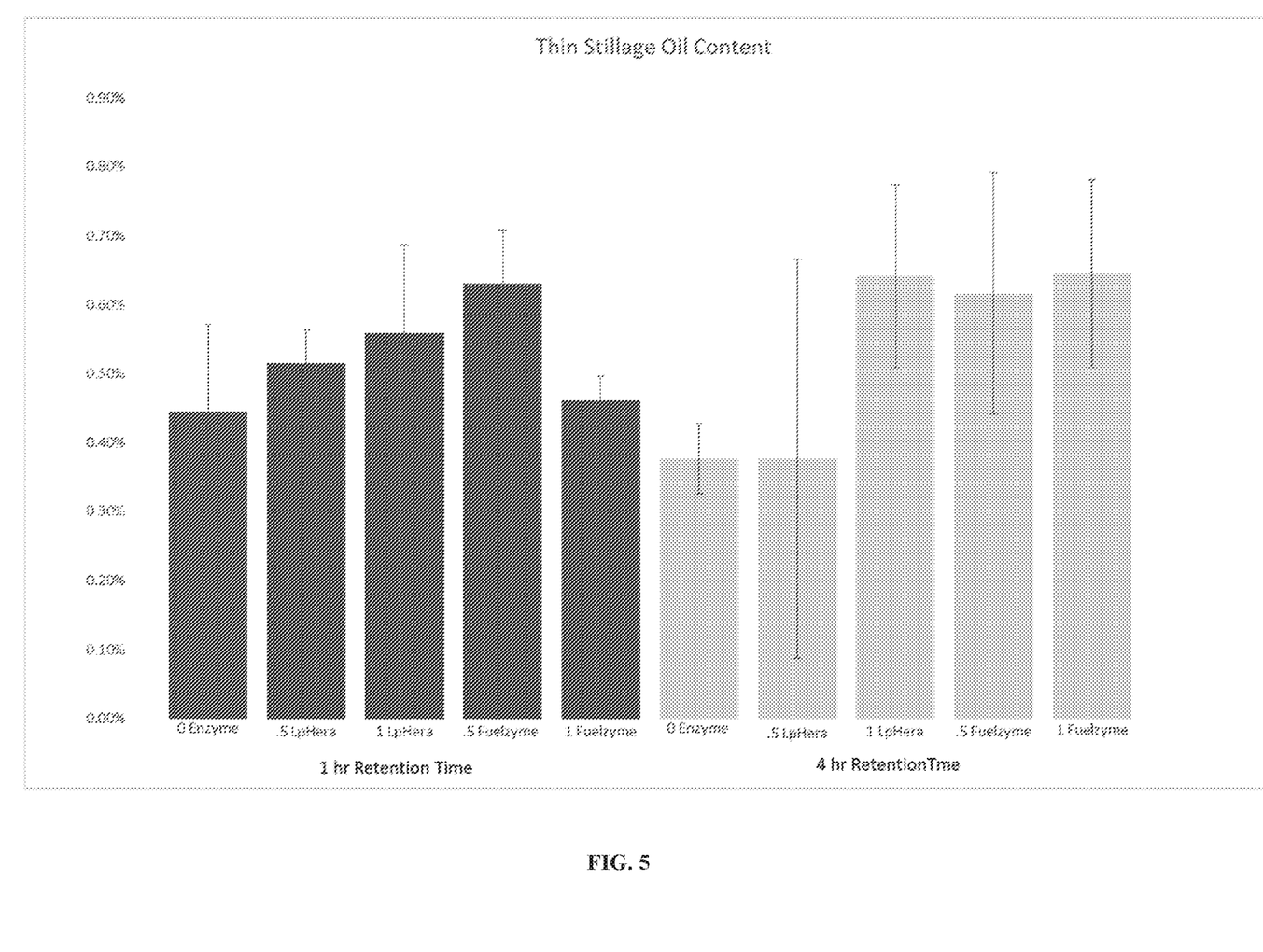
FIG. 5 is a graphical representation of a comparison of oil content (w/w %) for one hour and four hours.

Alpha amylases of varying amounts were added to the whole stillage obtained from a BPX™ process, dry grind, corn ethanol process. The alpha amylase was added into the whole stillage for 1 hour or 4 hours. Alpha amylase, LpHERA™ (Novozymes) and FUELZYMES™ (Verenium Corp, part of BASF) were each added at a 1.0× loading as noted in Example 1. The whole stillage is centrifuged to produce thin stillage. Through a series of evaporations and centrifugations, the oil was extracted from 30 ml of thin stillage. The thin stillage was washed three times with 15 ml each of hexane. The hexane was evaporated and the resulting oil residue weighed. The resultant oil (w/w %.) is shown in FIG. 5.

Example 3

Oil Yield in a Continuous Flow Process Over Extended Time Period

Alpha amylase enzyme was added to a tank with whole stillage in a continuous flow process over an extended time period. The whole stillage was from a BPX™ process, dry grind, and corn ethanol process. During the first eight months no enzyme was added. Alpha amylase was added over the next five months in varying amounts from 0.5× to 2× loading as noted in Example 1 and the loading amounts shown in Table 1.

When added into the whole stillage, the enzyme was added with a one hour residence time at doses noted in Table 1 and at a rate of 2 L/hour to 8 L/hour in a continues flow process. Alpha amylase used was FUELZYMES™ (Verenium Corp, part of BASF).

After the enzyme treatment, the whole stillage was further processed to result in thin stillage. Oil was extracted from the thin stillage in a process disclosed in U.S. Pat. No. 8,702,819.

TABLE 1

| Month | Enzyme loading | lb/bu oil production |
|---|---|---|
| 1. |  | 0.97 |
| 2. |  | 0.71 |
| 3. |  | 0.96 |
| 4. |  | 1.10 |
| 5. |  | 0.92 |
| 6. |  | 1.04 |
| 7. |  | 0.97 |
| 8. |  | 1.03 |
| 9. | 0.5X | 1.13 |
| 10. | — | 1.04 |
| 11. | 2.0X | 1.12 |
| 12. | 1.5X | 1.13 |
| 13. | 1X | 1.13 |

Figure 6:
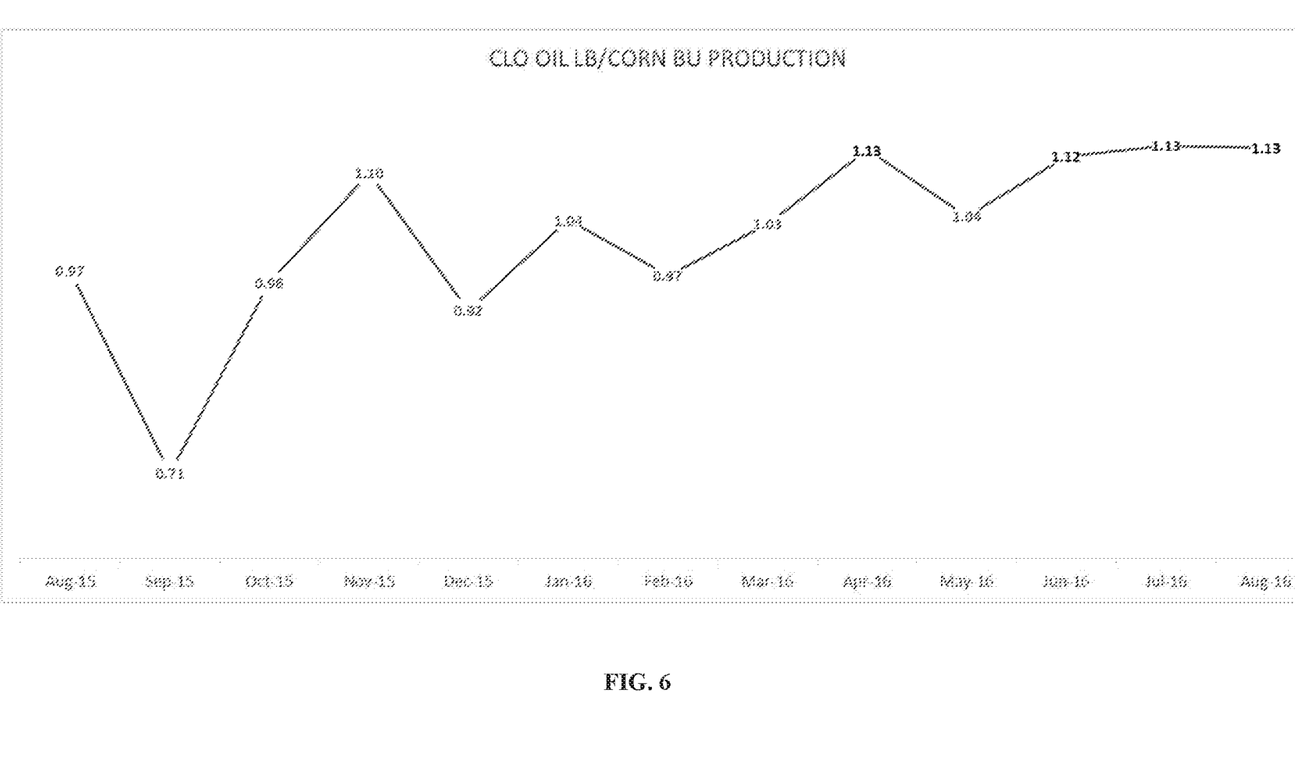
FIG. 6 is a graphical representation showing the yield of the oil production over an extended time period with and without amylase.

The data in Table 1 is also shown in FIG. 6. As seen from Table 1 and FIG. 6, when no enzyme was added (August 2015-March 2016), the average oil production was 0.97 lb/corn bushel. When enzyme was added, a 16% increase in oil production to 1.12 to 1.13 lb/corn was observed. When the enzyme was not added during the enzyme-addition period (i.e. May 2016), the oil production dropped to 1.04 lb/corn bushel.

Some additional non-limiting embodiments are provided below to further exemplify the present disclosure:
1. A method of obtaining an oil composition from a stillage composition comprising:
   adding one or more alpha amylase enzymes to a first stillage composition to form a second stillage composition, wherein the one or more enzymes are added to the first stillage composition at a pH of less than 4.2; and obtaining oil from the second stillage composition.

2. The method of embodiment 1, wherein the one or more alpha amylase enzymes are added to the first stillage composition at a pH of less than 4.0
3. The method of embodiment 1, wherein the one or more alpha amylase enzymes are added to the first stillage composition at a pH from 3.2 to 3.9.
4. The method of embodiment 1, wherein the one or more alpha amylase enzymes are added to the first stillage composition in an amount from 0.001 to 0.05 grams/100 grams of solids of the first stillage composition.
5. The method of embodiment 1, wherein the one or more alpha amylase enzymes are added to the first stillage composition in an amount from 0.002 to 0.04 grams/100 grams of solids of the first stillage composition.
6. The method of embodiment 1, wherein the one or more alpha amylase enzymes are added to the first stillage composition in an amount from 0.005 to 0.009 grams/100 grams of solids of the first stillage composition.
7. The method of embodiment 1, wherein the first stillage composition comprises whole stillage, thin stillage, wet cake and/or syrup.
8. The method of embodiment 1, wherein the first stillage composition is thin stillage.
9. The method of any one of the preceding embodiments, wherein the one or more alpha amylase enzymes are added to the first stillage composition at a temperature of 75 to 95 degrees Celsius.
10. The method of embodiment 1, wherein the oil obtained from the second stillage composition comprises:
   (a) adjusting pH of the second stillage composition into a first oil fraction to separate the first oil fraction into a second oil fraction and a second aqueous fraction; and
   (b) separating the second oil fraction to provide the oil composition.
11. A method of obtaining an oil composition from a stillage composition comprising:
   (a) separating a whole stillage into a thin stillage and a wet cake;
   (b) evaporating at least a portion of water from the thin stillage to condense the thin stillage into a syrup;
   (c) separating the syrup into a first oil fraction and a first aqueous fraction;
   (d) adjusting pH of the first oil fraction to separate the first oil fraction into a second oil fraction and a second aqueous fraction; and
   (e) separating the second oil fraction to provide the oil composition; wherein one or more alpha amylase enzymes are added to the whole stillage, thin stillage, wet cake and/or syrup in an amount from 0.001 to 0.05 grams/100 grams of solids of the whole stillage, thin stillage, wet cake and/or syrup.
12. The method of embodiment 11, wherein the one or more alpha amylase enzymes are added to the whole stillage, thin stillage, wet cake and/or syrup at a pH less than 4.2.
13. The method of embodiment 11, wherein the one or more alpha amylase enzymes are added to the whole stillage, thin stillage, wet cake and/or syrup at a pH less than 4.0.
14. The method of embodiment 11, wherein the one or more alpha amylase enzymes are added to the whole stillage, thin stillage, wet cake and/or syrup at a pH from 3.2 to 3.9.
15. The method of any one of the preceding embodiments, wherein the one or more alpha amylase is added to the whole stillage, thin stillage, wet cake and/or syrup at a temperature of 75 to 95 degrees Celsius.
16. The method of embodiment 11, wherein the one or more alpha amylase enzymes are added to the whole stillage, thin stillage, wet cake and/or syrup in an amount from 0.002 to 0.04 grams/100 grams of solids of the whole stillage, thin stillage, wet cake and/or syrup.

17. The method of embodiment 11, wherein the one or more alpha amylase enzymes are added to the whole stillage, thin stillage, wet cake and/or syrup in an amount from 0.005 to 0.009 grams/100 grams of solids of the whole stillage, thin stillage, wet cake and/or syrup.

18. The method of embodiment 11 further comprising steps before step a) of embodiment 11, the method comprising:
    a) converting a starch-containing material into glucose;
    b) fermenting the glucose in presence of a microorganism under conditions which produce beer;
    c) adjusting pH of the beer to pH less than 4.2; and
    d) recovering ethanol and a whole stillage from the beer.

19. The method of embodiment 18, wherein the pH of the beer is adjusted to a pH less than 4.0.

20. The method of embodiment 18, wherein the pH of the beer is adjusted to a pH from 3.2 to 3.9.

21. The method of embodiment 18, wherein the starch-containing material comprises cereal grains.

22. The method of embodiment 18, wherein the starch-containing material comprise wheat, barley, cassava, corn, rye, rice, sorghum (milo), millet, starchy root crops, tubers, or roots such as sweet potato and cassava, or any combinations thereof.

23. The method of embodiment 18, wherein the converting the starch-containing material into glucose of step (a) is without liquefaction step.

24. A system for obtaining oil from a stillage composition comprising:
    a first separator configured to separate a whole stillage into a first solid component and a first liquid portion;
    an evaporator in fluid communication with a first separator to receive the first liquid portion and configured to condense the first liquid portion;
    a second separator in fluid communication with the evaporator and configured to separate the condensed first liquid portion to a first aqueous fraction and a first oil fraction;
    a source of one or more alpha amylase enzymes in fluid communication with the first separator and second separator, wherein the one or more alpha amylase enzymes are added to the whole stillage, first liquid portion and/or condensed first liquid portion in an amount from 0.001 to 0.05 grams/100 grams of solids to the whole stillage, first liquid portion and/or condensed first liquid portion;
    a source of base in fluid communication with the first oil fraction; and
    a third separator in fluid communication with the first oil fraction and configured to obtain a second oil fraction from the pH adjusted first oil fraction.

25. The system of embodiment 24, wherein the one or more alpha amylase enzymes are added to the whole stillage, thin stillage, wet cake and/or syrup in an amount from 0.002 to 0.04 grams/100 grams of solids.

26. The system of embodiment 24, wherein the one or more alpha amylase enzymes are added to the whole stillage, thin stillage, wet cake and/or syrup in an amount from 0.005 to 0.009 grams/100 grams of solids.

27. The system of embodiment 24, wherein the alpha amylase is added to the whole stillage, first liquid portion and/or condensed first liquid portion at a pH less than 4.2.

28. The system of embodiment 24, wherein the alpha amylase is added to the whole stillage, first liquid portion and/or condensed first liquid portion at a pH less than 4.0.

29. The system of embodiment 24, wherein the alpha amylase is added to the whole stillage, first liquid portion and/or condensed first liquid portion at a pH from 3.2 to 3.9.

30. The system of embodiment 24, wherein the first solids component comprises wet cake.

31. The system of embodiment 24, wherein the first liquid portion comprises thin stillage.

32. The system of embodiment 24, wherein the first oil fraction is adjusted to a pH from 7 to 10.

33. The system of embodiment 24, wherein the system further comprises:
    a feedstock preparation system for receiving incoming feedstock and water and freeing sugar from the feedstock;
    a fermentation system located downstream from the feedstock preparation system for receiving the feedstock after the feedstock has been treated in the preparation system and for fermenting the sugar freed from the feedstock and producing beer which includes ethanol and feedstock; and
    a distillation system located downstream of the fermenting system for separating ethanol from the feedstock and producing ethanol and whole stillage.

What is claimed is:

1. A method of obtaining an oil composition from a stillage composition comprising:
    adding one or more alpha amylase enzymes to a first post-distillation stillage composition;
    exposing the first post-distillation stillage composition with the one or more alpha amylase enzymes to conditions comprising a pH of less than 4.2 and at a temperature of at least 75 degrees Celsius to form a second post-distillation stillage composition, wherein the one or more alpha amylase enzymes are added to the first post-distillation stillage composition in an amount from 0.001 to 0.05 grams/100 grams of solids of the first post-distillation stillage composition and to hydrolyze starch; and
    obtaining oil composition from the second post-distillation stillage composition.

2. The method of claim 1, wherein the one or more alpha amylase enzymes are added to the first stillage composition in an amount from 0.002 to 0.04 grams/100 grams of solids of the first post-distillation stillage composition.

3. The method of claim 1, wherein the one or more alpha amylase enzymes are added to the first stillage compositing in an amount from 0.005 to 0.009 grams/100 grams of solids of the first post-distillation stillage composition.

4. The method of claim 1, wherein the one or more alpha amylase enzymes are added to the first stillage composition at a pH of less than 4.0.

5. The method of claim 1, wherein the one or more alpha amylase enzymes are added to the first stillage composition at a pH from 3.2 to 3.9.

6. The method claim 1, wherein the first post-distillation stillage composition comprises whole stillage, thin stillage, wet cake and/or syrup.

7. The method of claim 1, wherein the first stillage composition is thin stillage.

8. The method of claim 1, wherein the one or more alpha amylase enzymes are added to the first post-distillation stillage composition at a temperature of 75 to 95 degrees Celsius.

9. The method of claim 1, wherein obtaining oil composition from the second post-distillation stillage composition comprises 15 wt % to 75 wt % more oil compared to a stillage composition in which no alpha amylase is added.

10. The method of claim 1, wherein obtaining oil composition from the second stillage composition comprises 30 wt % to 50 wt % more oil compared to a stillage composition in which no alpha amylase is added.

11. The method of claim 6 further comprising:
separating the whole stillage into the thin stillage and the wet cake; and
evaporating at least a portion of water from the thin stillage to condense the thin stillage into the syrup.

12. The method of claim 11 wherein obtaining oil composition comprises:
separating the syrup into a first oil fraction and a first aqueous fraction;
adjusting pH of the first oil fraction to separate the first oil fraction into a second oil fraction and a second aqueous fraction; and
separating the second oil fraction to provide the oil composition.

13. The method of claim 6, wherein the one or more alpha amylase enzymes are added to the whole stillage in an amount from 0.001 to 0.05 grams/100 grams of solids of the whole stillage.

14. A method of obtaining an oil composition comprising:
adding one or more alpha amylase enzymes to a beer;
wherein the one or more alpha amylase enzymes are added to the beer in an amount from 0.001 to 0.05 grams/100 grams of solids of the beer and to hydrolyze starch;
distilling the beer to obtain alcohol and whole stillage;
separating the whole stillage to produce thin stillage and wet cake; and
obtaining oil composition from thin stillage.

15. The method of claim 14 further comprising:
evaporating at least a portion of water from the thin stillage to condense the thin stillage into syrup.

16. The method of claim 15 further comprising:
separating the syrup into a first oil fraction and a first aqueous fraction;
adjusting pH of the first oil fraction to separate the first oil fraction into a second oil fraction and a second aqueous fraction; and
separating the second oil fraction to provide the oil composition.

17. The method of claim 14, wherein the one or more alpha amylase enzymes are added to the whole stillage in an amount from 0.001 to 0.05 grams/100 grams of solids of the whole stillage.

18. The method of claim 14, wherein the beer is made by a method comprising:
i. milling grain to provide a milled grain, wherein the grain comprises starch;
ii. hydrolyzing starch to produce lower molecular weight sugars; and
iii. fermenting the lower molecular weight sugars with a yeast to produce the beer.

* * * * *